US010300001B2

(12) United States Patent
Gershon et al.

(10) Patent No.: US 10,300,001 B2
(45) Date of Patent: May 28, 2019

(54) IMPLEMENTING ORGANIC MATERIALS IN SUNSCREEN APPLICATIONS

(71) Applicant: International Business Machines Corporation, Armonk, NY (US)

(72) Inventors: Talia S. Gershon, White Plains, NY (US); Ning Li, Yorktown Heights, NY (US); Devendra K. Sadana, Yorktown Heights, NY (US); Teodor K. Todorov, Yorktown Heights, NY (US)

(73) Assignee: International Business Machines Corporation, Armonk, NY (US)

(*) Notice: Subject to any disclaimer, the term of this patent is extended or adjusted under 35 U.S.C. 154(b) by 105 days.

(21) Appl. No.: 15/409,883

(22) Filed: Jan. 19, 2017

(65) Prior Publication Data

US 2017/0128343 A1    May 11, 2017

Related U.S. Application Data

(62) Division of application No. 15/082,669, filed on Mar. 28, 2016, now Pat. No. 9,883,994.

(Continued)

(51) Int. Cl.
*A61K 8/02* (2006.01)
*A61K 8/27* (2006.01)
(Continued)

(52) U.S. Cl.
CPC ............ *A61K 8/494* (2013.01); *A61K 8/0216* (2013.01); *A61K 8/0241* (2013.01); *A61K 8/27* (2013.01);
(Continued)

(58) Field of Classification Search
None
See application file for complete search history.

(56) References Cited

U.S. PATENT DOCUMENTS

| 3,761,261 A | 9/1973 | Ono et al. |
| 3,863,007 A | 1/1975 | Warner, Jr. |

(Continued)

FOREIGN PATENT DOCUMENTS

| CN | 103071535 A | 5/2013 |
| CN | 104609459 A | 5/2015 |

(Continued)

OTHER PUBLICATIONS

Latha et al. "Sunscreening Agents: A review," Journal of Clinical and Aesthetic Dermatology 6(1):16-26, 2013.*

(Continued)

*Primary Examiner* — Ileana Popa
*Assistant Examiner* — Alissa Prosser
(74) *Attorney, Agent, or Firm* — Ryan, Mason & Lewis, LLP

(57) ABSTRACT

Techniques for implementing organic materials in sunscreen applications are provided herein. A method includes selecting a combination of multiple organic materials to incorporate into a sunscreen composition, wherein said selecting is based on (i) a desired absorption spectrum of the sunscreen composition, (ii) the absorption spectrum of each of the multiple organic materials, and (iii) a particle size limitation for each of the multiple organic materials, and incorporating the selected combination of organic materials into the sunscreen composition to generate the desired absorption spectrum. A composition includes a combination of multiple organic materials incorporated into a sunscreen composition, wherein the combination of organic materials is selected based on (i) a desired absorption spectrum of the sunscreen composition, (ii) the absorption spectrum of each of the multiple organic materials, and (iii) a particle size limitation for each of the multiple organic materials.

16 Claims, 3 Drawing Sheets

Related U.S. Application Data

(60) Provisional application No. 62/213,715, filed on Sep. 3, 2015.

(51) Int. Cl.
  *A61K 8/41* (2006.01)
  *A61K 8/49* (2006.01)
  *A61Q 17/04* (2006.01)

(52) U.S. Cl.
  CPC .............. *A61K 8/416* (2013.01); *A61Q 17/04* (2013.01); *A61K 2800/26* (2013.01); *A61K 2800/412* (2013.01); *A61K 2800/413* (2013.01); *A61K 2800/42* (2013.01); *A61K 2800/805* (2013.01)

(56) References Cited

U.S. PATENT DOCUMENTS

| | | | |
|---|---|---|---|
| 4,549,195 A | 10/1985 | Bluzer | |
| 5,011,782 A | 4/1991 | Lamb | |
| 5,030,669 A * | 7/1991 | Hendrickson | B01F 3/04439 |
| | | | 106/412 |
| 5,147,125 A | 9/1992 | Austin | |
| 5,223,250 A | 6/1993 | Mitchell | |
| 5,441,726 A | 8/1995 | Mitchnick | |
| 5,534,056 A | 7/1996 | Kuehnle | |
| 5,553,630 A | 9/1996 | Dupuis et al. | |
| 5,902,569 A | 5/1999 | Oshima | |
| 6,419,909 B1 | 7/2002 | Lorant | |
| 6,534,044 B1 | 3/2003 | Wada | |
| 7,241,399 B2 | 7/2007 | Haubold | |
| 7,514,863 B2 * | 4/2009 | Lee | B82Y 10/00 |
| | | | 313/504 |
| 8,647,373 B1 * | 2/2014 | Shepherd | A61N 5/0613 |
| | | | 607/88 |
| 9,056,063 B2 | 6/2015 | Hanson | |
| 9,144,535 B1 | 9/2015 | Daly et al. | |
| 9,144,536 B1 | 9/2015 | Daly et al. | |
| 9,773,931 B2 | 9/2017 | Hossain | |
| 2002/0122832 A1 | 9/2002 | Hanke | |
| 2003/0102099 A1 | 6/2003 | Yadav | |
| 2004/0209081 A1 | 10/2004 | Hagihara | |
| 2005/0008861 A1 | 1/2005 | Yadav et al. | |
| 2005/0048010 A1 | 3/2005 | Kliss | |
| 2005/0208005 A1 | 9/2005 | Giroud | |
| 2005/0227063 A1 | 10/2005 | Lawandy | |
| 2005/0238600 A1 | 10/2005 | Lien | |
| 2005/0265935 A1 | 12/2005 | Hollingsworth | |
| 2006/0228310 A1 | 10/2006 | Lyth | |
| 2006/0270053 A1 | 11/2006 | Tilak | |
| 2007/0280895 A1 | 12/2007 | Weimer | |
| 2008/0149850 A1 | 6/2008 | Tardif et al. | |
| 2008/0220026 A1 | 9/2008 | Maltra | |
| 2009/0022765 A1 | 1/2009 | Chung et al. | |
| 2009/0104130 A1 | 4/2009 | Bernstein | |
| 2009/0258072 A1 | 10/2009 | Schlossman | |
| 2009/0258230 A1 | 10/2009 | Schlossman | |
| 2010/0008872 A1 | 1/2010 | Katusic | |
| 2010/0040567 A1 | 2/2010 | Katusic | |
| 2010/0055138 A1 | 3/2010 | Margulies | |
| 2010/0310871 A1 | 12/2010 | McCormick | |
| 2011/0268678 A1 | 11/2011 | Armstrong | |
| 2013/0006118 A1 * | 1/2013 | Pan | A61N 5/0616 |
| | | | 600/476 |
| 2013/0039858 A1 * | 2/2013 | Brown | G01N 33/54346 |
| | | | 424/9.3 |
| 2013/0216834 A1 | 8/2013 | Hashimoto | |
| 2014/0142213 A1 | 5/2014 | Weiss | |
| 2015/0283059 A1 | 10/2015 | Nagare | |
| 2016/0082513 A1 | 3/2016 | Niedermeyer | |

FOREIGN PATENT DOCUMENTS

| | | | | |
|---|---|---|---|---|
| EP | 1889810 A1 | 2/2008 | | |
| JP | 09059591 A | 3/1997 | | |
| JP | 2008024677 A | 2/2008 | | |
| JP | 2011102291 A | 5/2011 | | |
| WO | 2005023535 A2 | 3/2005 | | |
| WO | 2008017176 A2 | 2/2008 | | |
| WO | 2008079758 A1 | 7/2008 | | |
| WO | 2011004133 A2 | 1/2011 | | |
| WO | WO-2011089571 A2 * | 7/2011 | ........... | A61K 8/0241 |
| WO | 2012046204 A1 | 4/2012 | | |
| WO | 2013040149 | 3/2013 | | |
| WO | 2013094639 A1 | 6/2013 | | |
| WO | WO-2014040177 A1 * | 3/2014 | ............ | A61Q 19/08 |
| WO | 2014049139 A1 | 4/2014 | | |
| WO | 2014077189 | 5/2014 | | |
| WO | 2016020168 A1 | 2/2016 | | |

OTHER PUBLICATIONS

Sreejith et al. "Squaraine dyes: a mine of molecular materials," Journal of Materials Chemistry 18:264-274, 2008.*
Smijs et al. Titanium Dioxide and Zinc Oxide Nanoparticles in Sunscreens: Focus on Their Safety and Effectiveness, Nanotechnology, Science and Applications 4:95-112, Oct. 2011.
Wikipedia, List of Refractive Indices, last modified Feb. 15, 2017; https://en.wikipedia.org/wiki/List_of_refractive_indices.
Ultraviolet Radiation and the INTERSUN Programme [online]. WHO, Nov. 2003 [retrieved on Jun. 8, 2017]. Retrieved from the internet <http://www.who.int/uv/uv_and_health/en/>.
English language translation of WO 2013 094639 (A1) (Year: 2013).
Family Health Team, "Best Ways to Protect Your Hair From Sun Damage," Cleveland Clinic, health essentials, <https://health.clevelandclinic.org/2014/08/best-ways-to-protect-your-hair-from-sun-damage/>, published Aug. 22, 2014, p. 1-4.
Machine translation WO 2011/004133, printed 2017.
Wikipedia "Band Gap" last modified Jul. 18, 2017, https://en.wikipedia.org/wiki/Band_gap.
Machine translation WO 2012/046204, printed 2017.
Naylor et al. "Sunscreens," accessed 2017, http://telemedicine.org/sundam/sundam2.4.2.html.
Thokozane Moses Sithole, Synthesis and characterization of MBxOy:Eu (M=Ca, Sr, Ba) phosphors and TiO2 semiconductor for application in luminescence and energy materials, University of the Free State, Nov. 2014.
Sardar et al., Optical-absorption intensities and intermanifold emission cross sections of trivalent erbium ions in calcium fluorophosphate, Journal of Applied Physics, Sep. 2005.
Lu et al., 2008—White Up-Conversion Luminescence in Rare-Earth-Ion-Doped YAlO3 Nanocrystals, J. Phys. Chem. C 2008, 112, 15071-15074.
Refractive index of ZnO (Zinc oxide)—Bond-o, http://refractiveindex.info/?shelf=main&book=ZnO&page=Bond-o, Mar. 25, 2016.
Refractive index of SiO2 (Silicon dioxide, Silica, Quartz)—Malitson, http://refractiveindex.info/?shelf=main&book=SiO2&page=Malitson, Mar. 25, 2016.
Schubert et al., Design of multilayer antireflection coatings made from co-sputtered and low-refractive-index materials by genetic algorithm. Optics Express vol. 16, No. 8, 2008.
Law et al., ZnO—Al2O3 and ZnO—TiO2 Core-Shell Nanowire Dye-Sensitized Solar Cells. J. Phys. Chem. B 2006, 110, 22652-22663.
Pu et al., Core/shell structured ZnO/SiO2 nanoparticles: Preparation, characterization and photocatalytic property. Applied Surface Science 257 (2010) 393-397.
Mantz et al., Progress in Organic Coatings 47 (2003) 432-442, "A multiple-scattering model analysis of zinc oxide pigment for spacecraft thermal control coatings."
Song et al., Toxicology Letters 199 (2010) 389-397, "Role of the dissolved zinc io and reactive oxygen species in cytotoxicity of ZnO nanoparticles."

(56) References Cited

OTHER PUBLICATIONS

Bohren et al., "Absorption and Scattering of Light by Small Particles", Wiley-VCH, © 2004, Weinheim, Table of Contents.
Bae et al., J. Phys. Chem. B 2005, 109, 2526-2531, "Comparative Structure and Optical Properties of Ga-, In-, and Sn-Doped ZnO Nanowires Synthesized by thermal evaporation."
NanoComposix, Silver Nanoparticles: Optical Properties, http://nanocomposix.com/pages/silver-nanoparticles-optical-properties, Apr. 20, 2016.
Awazu et al., 2007—A Plasmonic Photocatalyst Consisting of Silver Nanoparticles Embedded in Titanium Dioxide, J. Am. Chem. Soc. 2008, 130, 1676-1680.
Sherry et al., Localized Surface Plasmon Resonance Spectroscopy of Single Silver Nanocubes, Nano Lett., vol. 5, No. 10, 2005.
Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.
Haynes et al., Nanosphere Lithography: Tunable Localized Surface Plasmon Resonance Spectra of Silver Nanoparticles, J. Phys. Chem. B 2000, 104, 10549-10556.
U. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.
Tsuzuki et al., Nanoparticle Coatings for UV Protective Textiles, RJTA vol. 14 No. 2 2010.
Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.
Li et al., 2011—Sol-gel preparation and characterization of nanoporous ZnO_SiO2 coatings with broadband antireflection properties, Applied Surface Science 257 (2011) 9752-9756.
Messaoudi et al., "Synthesis and characterization of ZnO/Cu2O core-shell nanowires grown by two-step electrodeposition method." Applied Surface Science 343 (2015) 148-152.
Luo et al., Facile synthesis of composition-tuned ZnO/ZnxCd1-xSe nanowires for photovoltaic applications, Nanoscale Research Letters (2015) 10:181.
List of IBM Patents or Applications Treated as Related.
Cuprous Oxide, Chemical Book, pp. 1-4, Accessed Sep. 18, 2017, https://www.chemicalbook.com/ProductChemicalPropertiesCB9853041_EN.htm.
Machine translation, JP 2008-024677, printer 2018.
Kelly et al. "The Optical Properties of Metal Nanoparticles: The Influence of Size, Shape and Dielectric Environment," Journal of Physical Chemistry B 107:668-677, 2003.
Garcia, "Surface Plasmons in Metallic Nanoparticles: Fundamentals and Applications," Journal of Physics D: Applied Physics 44(28), 283001, 2011.
Faure, B. et al. Dispersion and Surface Functionalization of Oxide Nanoparticles for Transparent Photocatalytic and UV-protecting Coatings and Sunscreens, Sci Technol. Adv. Mater. 14 2013, 023001.
Tariq Jan, et al. Sn Doping Induced Enhancement in the Activity of ZnO Nanostructures Against Antibiotic Resistant *S. aureus* Bacteria; Int J. Nanomedicine, vol. 8, pp. 3679-3687; Published online Sep. 30, 2013.
Bhatti et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, Issue 10; pp. 80-85; published Oct. 2015.
Simon Aldridge and Anthony Downs. The Group 13 Metals Aluminum, Gallium, Indium and Thallium Chemical Patterns and Peculiarities, 2011 John Wiley & Sons, Ltd., p. 623 (Year: 2011).
Merriam-Webster "Roughen." Merriam-Webster.com, Merriam-Webster, n.d. Web. Aug. 22, 2018 (Year: 2018).

\* cited by examiner

IMPLEMENTING ORGANIC MATERIALS IN SUNSCREEN APPLICATIONS

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Further, it is noted that some amount of high-energy light (for example, light within a wavelength range of approximately 270 nm to approximately 300 nm) is needed by the human body for producing vitamin D (which is useful, for example, in calcium absorption and bone growth). Accordingly, while existing sunscreen compositions are capable of blocking portions of UV light from passing through the composition to be absorbed by the skin of the user, such compositions simultaneously preclude the UV light responsible for aiding vitamin D production to be absorbed by the skin.

SUMMARY

In one embodiment of the present invention, techniques for implementing organic materials in sunscreen applications are provided. An exemplary method can include steps of selecting a combination of multiple organic materials to incorporate into a sunscreen composition, wherein said selecting is based on (i) a desired absorption spectrum of the sunscreen composition, (ii) the absorption spectrum of each of the multiple organic materials, and (iii) a particle size limitation for each of the multiple organic materials, and incorporating the selected combination of organic materials into the sunscreen composition to generate the desired absorption spectrum.

In another embodiment of the invention, a composition can include a combination of multiple organic materials incorporated into a sunscreen composition, wherein the combination of organic materials is selected based on (i) a desired absorption spectrum of the sunscreen composition, (ii) the absorption spectrum of each of the multiple organic materials, and (iii) a particle size limitation for each of the multiple organic materials.

These and other objects, features and advantages of the present invention will become apparent from the following detailed description of illustrative embodiments thereof, which is to be read in connection with the accompanying drawings.

DETAILED DESCRIPTION

As described herein, an embodiment of the present invention includes zinc oxide compositions, methods of fabrications thereof and methods of use thereof. Specifically, at least one embodiment of the invention includes techniques for implementing organic materials in sunscreen applications.

As further detailed herein, one or more embodiments of the invention include generating ZnO compositions and methods of use thereof for effectively blocking more and/or all of the complete spectrum of UV light (that is, as noted above, the UV radiation that is not absorbed by the ozone, and which ranges between approximately 280 nm and 400 nm). Additionally, one or more embodiments of the invention include generating ZnO compositions and methods of use thereof for permitting a specific range (or "windows") of light (radiation) to pass through a ZnO composition such that the specific range of light can be absorbed by the skin of a human user. For example, at least one embodiment of the invention can include generating a ZnO composition that allows radiation at 276 nm (which is the wavelength that facilitates vitamin D absorption in the skin) to pass through the composition to be absorbed by the skin, while blocking harmful UV radiation at other wavelengths.

At least one embodiment of the invention can include combining multiple organic materials with to create a sunscreen composition with a specific absorption spectrum. The absorption coefficient is typically much higher in organic material than in inorganic materials. Accordingly, in one or more embodiments of the invention, less of the organic materials would be necessary (than, for example, relevant inorganic materials) to achieve the same objective(s). For example, a combination of multiple organic materials, each having a specific absorption spectrum, can cover (that is, absorb) the entire UV spectrum. In one or more embodiments of the invention, example organic materials can include, but are not limited to, (i) tin(II) phthalocyanine (SnPc), (ii) chloroaluminum phthalocyanine (ClAlPc), (iii) squaraine (SQ), (iv) N,N'-Bis(naphthalen-1-yl)-N,N'-bis(phenyl)-2,2'-dimethylbenzidine (a-NPD), (v) N,N'-Bis(3-methylphenyl)-N,N'-bis(phenyl)-benzidine (TPD), (vi) 4,4',4"-Tris(N-3-methylphenyl-N-phenyl-amino)triphenylamine (MTDATA), etc.

Additionally, one or more embodiments of the invention can include implementing organic materials by themselves (that is, without any inorganic particles) to create a sunscreen composition. Alternatively, at least one embodiment of the invention can include implementing one or more organic materials as a coating applied to inorganic particles, such as ZnO, to create a sunscreen composition. Accordingly, by way of example, a combination of organic materials can be used to replace ZnO particles in a sunscreen composition and/or to supplement ZnO particles in a sunscreen composition.

Figure 1:
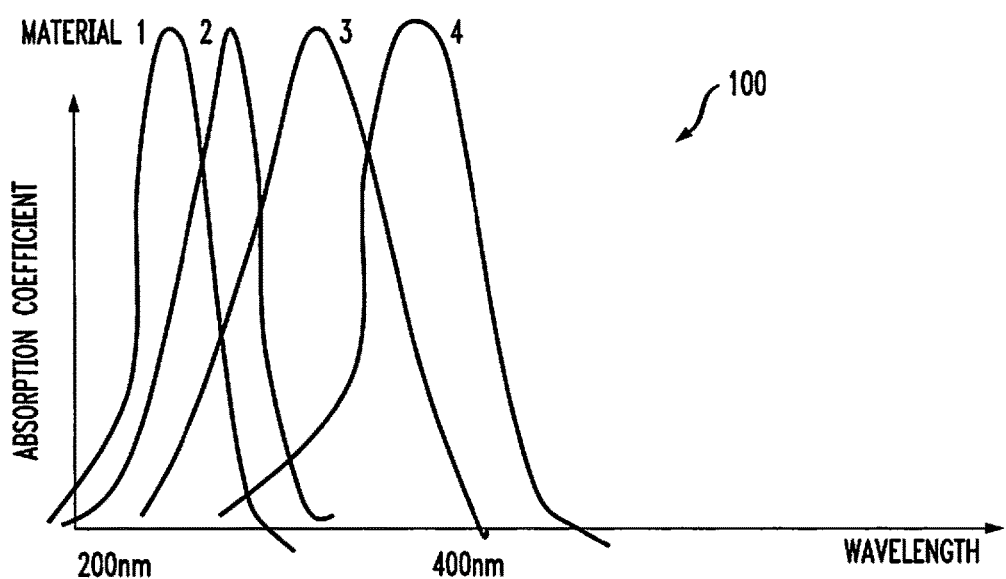
FIG. 1 is a graph illustrating absorption coefficients of four organic materials, according to an embodiment of the invention.

FIG. 1 is a graph 100 illustrating absorption coefficients of four organic materials, according to an embodiment of the invention. Based on the illustrated absorption coefficients of the four noted organic materials, the combination of these four materials can, for example, replace ZnO in a sunscreen composition, as this combination of organic materials covers and/or replicates the absorption spectrum of ZnO with respect to UV light.

Figure 2:
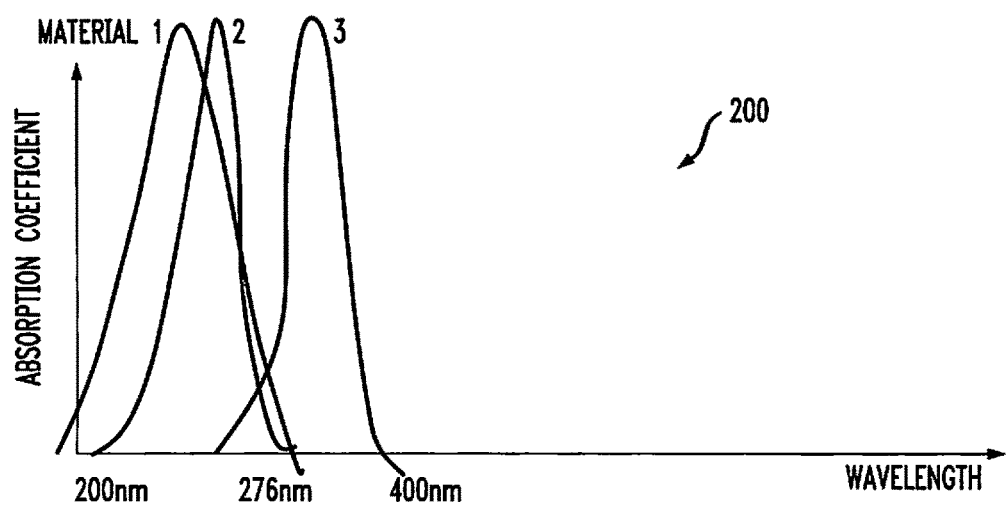
FIG. 2 is a graph illustrating absorption coefficients of three organic materials, according to an embodiment of the invention.

FIG. 2 is a graph 200 illustrating absorption coefficients of three organic materials, according to an embodiment of the invention. Specifically, the combination of organic materials illustrated in FIG. 2 is similar to the combination illustrated in FIG. 1, except that the organic material that absorbs light within the approximate wavelength of 276 nm has been removed from the combination. Consequently, such a combination can cover and/or replicate the absorption spectrum of ZnO with respect to UV light, while also permitting light to pass through (that is, not be absorbed) at a wavelength that will facilitate vitamin D production in the skin.

Figure 3A:
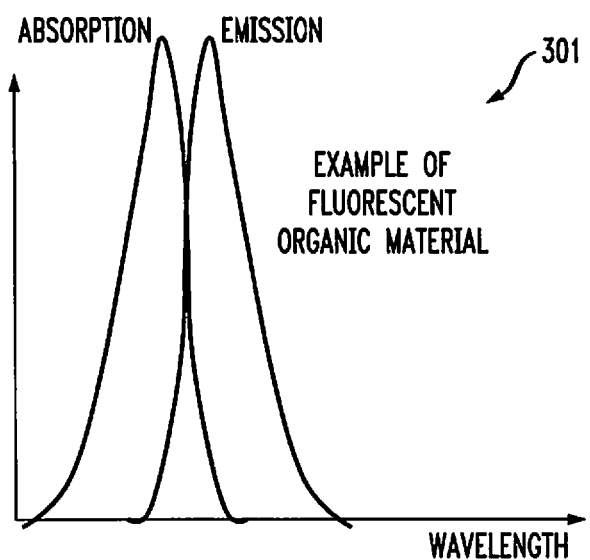
FIG. 3A and FIG. 3B are graphs illustrating absorption and emission coefficients of one or more organic materials, according to an embodiment of the invention.
Figure 3B:
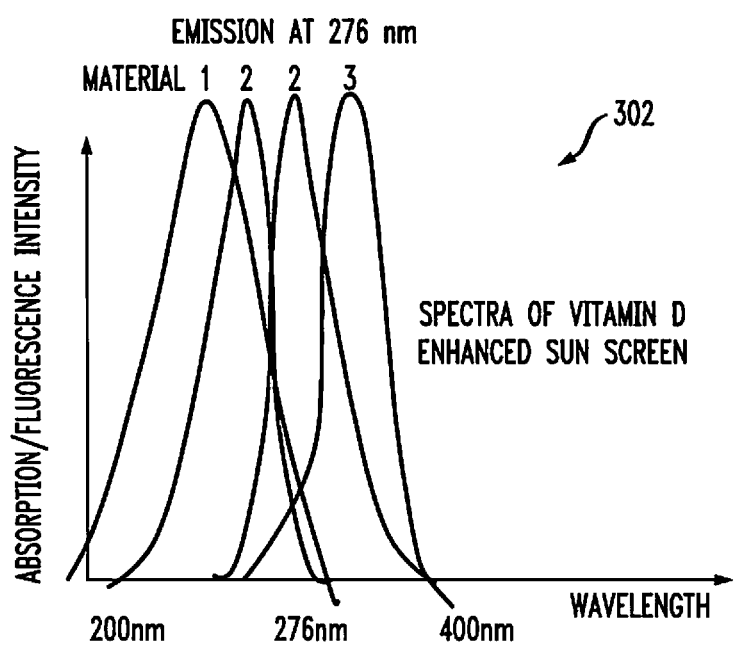

FIG. 3A and FIG. 3B are graphs (301 and 302, respectively) illustrating absorption and emission coefficients of one or more organic materials, according to an embodiment of the invention. It is to be appreciated that light absorbed by an organic material (such as those depicted in FIG. 3A and FIG. 3B) is emitted by that organic material at a higher wavelength (than is absorbed).

In at least one embodiment of the invention, organic fluorescent material (that is, light that is emitted after being absorbed) can be used to enhance vitamin D wavelength (at 276 nm, for instance) light intensity. It is noted that the wavelength of a fluorescent organic material is typically approximately 20 nm longer than the corresponding absorption wavelength. Accordingly, compositions can be designed using materials that emit at desired wavelengths to accentuate and/or emphasize certain optical effects or characteristics. As depicted, for example, in FIG. 3B, emission from material 2, which includes light at 276 nm, can be utilized in conjunction with a lack of material which absorbs light at 276 nm to create a sunscreen composition that emphasizes the passing of light at 276 nm so as to facilitate vitamin D production in the skin of the user.

Figure 4:
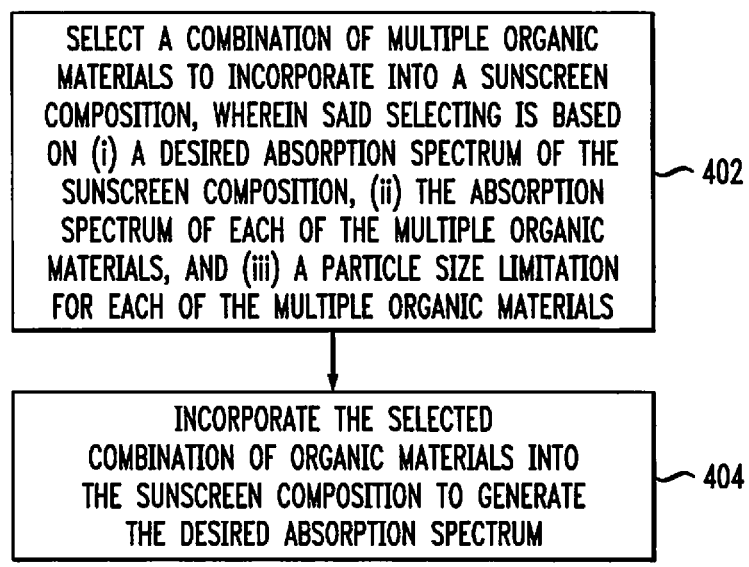
FIG. 4 is a flow diagram illustrating techniques, according to an embodiment of the invention.

FIG. 4 is a flow diagram illustrating techniques according to an embodiment of the present invention. Step 402 includes selecting a combination of multiple organic materials to incorporate into a sunscreen composition, wherein said selecting is based on (i) a desired absorption spectrum of the sunscreen composition, (ii) the absorption spectrum of each of the multiple organic materials, and (iii) a particle size limitation for each of the multiple organic materials. In one or more embodiments of the invention, the desired absorption spectrum of the sunscreen composition can include the spectrum of ultraviolet light. In such an embodiment, each of the multiple organic materials can have an absorption spectrum that covers a portion of the spectrum of ultraviolet light. Additionally, in at least one embodiment of the invention, the desired absorption spectrum of the sunscreen composition can include the spectrum of ultraviolet light outside of the portion of the spectrum of ultraviolet light responsible for facilitating vitamin D production.

The selecting step can further be based on the color that each of the multiple organic materials affect upon the sunscreen composition. In one or more related embodiments of the invention, depending upon the color affected upon the sunscreen composition, such a composition can serve the function as a makeup. Also, in one or more embodiments of the invention, the selecting step can be further based on the emission spectrum of each of the multiple organic materials. In such an embodiment, the desired absorption spectrum of the sunscreen composition can include the spectrum of ultraviolet light outside of the portion of the spectrum of ultraviolet light responsible for facilitating vitamin D production, and at least one of the multiple organic materials can have an emission spectrum that covers the portion of the spectrum of ultraviolet light responsible for facilitating vitamin D production.

In one or more embodiments of the invention, the organic materials can include (i) tin(II) phthalocyanine, (ii) chloroaluminum phthalocyanine, (iii) squaraine, (iv) N,N'-Bis(naphthalen-1-yl)-N,N'-bis(phenyl)-2,2'-dimethylbenzidine, (v) N,N'-Bis(3-methylphenyl)-N,N'-bis(phenyl)-benzidine, and/or (vi) 4,4',4"-Tris(N-3-methylphenyl-N-phenyl-amino)triphenylamine.

Additionally, in one or more embodiments of the invention, the particle size limitation comprises a limitation of less than two hundred nanometers to reduce Rayleigh scattering and reduce whitening of the sunscreen composition. Also, such an embodiment can further include embedding the organic materials in a particle of a size that is greater than two hundred nanometers, such that optical spacing is maintained between the organic materials (to reduce scattering). Alternatively, such an embodiment can additionally include attaching the organic materials to a particle of a size that is greater than two hundred nanometers, such that optical spacing is maintained between the organic materials (to reduce scattering).

Step 404 includes incorporating the selected combination of organic materials into the sunscreen composition to generate the desired absorption spectrum. Additionally, the techniques depicted in FIG. 4 can also include applying the selected combination of organic materials as a coating to the surface of each of one or more zinc oxide particles within the sunscreen composition.

Also, an additional embodiment of the invention includes a composition that includes a combination of multiple organic materials incorporated into a sunscreen composition, wherein the combination of organic materials is selected based on (i) a desired absorption spectrum of the sunscreen composition, (ii) the absorption spectrum of each of the multiple organic materials, and (iii) a particle size limitation for each of the multiple organic materials. In such a composition, the combination of organic materials can optionally be applied as a coating to the surface of each of one or more zinc oxide particles within the sunscreen composition.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, implementing a combination of multiple organic materials to create a composition that can absorb the entire UV spectrum.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
    selecting a combination of multiple organic materials to incorporate into a sunscreen composition, wherein said selecting is based at least in part on (i) a desired absorption spectrum of the sunscreen composition, (ii) the absorption spectrum of each of the multiple organic materials, and (iii) a particle size limitation for each of the multiple organic materials, and wherein the multiple organic materials comprise N,N'-Bis(naphthalen-1-yl)-N,N'-bis(phenyl)-2,2'-dimethylbenzidine; and
    incorporating the selected combination of organic materials into the sunscreen composition to generate the desired absorption spectrum.

2. The method of claim 1, wherein each of the multiple organic materials comprises a particle size of less than two hundred nanometers.

3. The method of claim 2, further comprising:
    embedding the multiple organic materials in a particle of a size that is greater than two hundred nanometers, such that optical spacing is maintained between the multiple organic materials.

4. The method of claim 2, further comprising:
    attaching the multiple organic materials to a particle of a size that is greater than two hundred nanometers, such that optical spacing is maintained between the multiple organic materials.

5. The method of claim 1, wherein said selecting is further based on the color that each of the multiple organic materials affect upon the sunscreen composition.

6. The method of claim 1, wherein the multiple organic materials further comprise tin(II) phthalocyanine.

7. The method of claim 1, wherein the multiple organic materials further comprise chloroaluminum phthalocyanine.

8. The method of claim 1, wherein the multiple organic materials further comprise squaraine.

9. The method of claim 1, further comprising:
    applying the selected combination of multiple organic materials as a coating to the surface of each of one or more zinc oxide particles within the sunscreen composition.

10. The method of claim 1, wherein the desired absorption spectrum of the sunscreen composition comprises the spectrum of ultraviolet light.

11. The method of claim 1, wherein the desired absorption spectrum of the sunscreen composition comprises the spectrum of ultraviolet light outside of the portion of the spectrum of ultraviolet light responsible for facilitating vitamin D production.

12. The method of claim 1, wherein said selecting is further based on the emission spectrum of each of the multiple organic materials.

13. The method of claim 12, wherein the desired absorption spectrum of the sunscreen composition comprises the spectrum of ultraviolet light outside of the portion of the spectrum of ultraviolet light responsible for facilitating vitamin D production.

14. The method of claim 13, wherein at least one of the multiple organic materials has an emission spectrum that covers the portion of the spectrum of ultraviolet light responsible for facilitating vitamin D production.

15. A method, comprising:
    selecting a combination of multiple organic materials to incorporate into a sunscreen composition, wherein said selecting is based at least in part on (i) a desired absorption spectrum of the sunscreen composition, (ii) the absorption spectrum of each of the multiple organic materials, and (iii) a particle size limitation for each of the multiple organic materials, and wherein the multiple organic materials comprise N,N'-Bis(3-methylphenyl)-N,N'-bis(phenyl)-benzidine; and
    incorporating the selected combination of organic materials into the sunscreen composition to generate the desired absorption spectrum.

16. A method, comprising:
    selecting a combination of multiple organic materials to incorporate into a sunscreen composition, wherein said selecting is based at least in part on (i) a desired absorption spectrum of the sunscreen composition, (ii) the absorption spectrum of each of the multiple organic materials, and (iii) a particle size limitation for each of the multiple organic materials, and wherein the multiple organic materials comprise 4,4',4"-Tris(N-3-methylphenyl-N-phenyl-amino)triphenylamine; and
    incorporating the selected combination of organic materials into the sunscreen composition to generate the desired absorption spectrum.

* * * * *